US011986021B2

(12) United States Patent
Pohl et al.

(10) Patent No.: US 11,986,021 B2
(45) Date of Patent: May 21, 2024

(54) ELECTRONIC INHALATION APPARATUS WITH A CHIP MODULE FIXED WITH A FOLDING STRUCTURE

(71) Applicant: Infineon Technologies AG, Neubiberg (DE)

(72) Inventors: Jens Pohl, Bernhardswald (DE); Thea Goetz, Regensburg (DE); Frank Pueschner, Kelheim (DE); Thomas Spoettl, Mintraching (DE)

(73) Assignee: Infineon Technologies AG, Neubiberg (DE)

( * ) Notice: Subject to any disclaimer, the term of this patent is extended or adjusted under 35 U.S.C. 154(b) by 462 days.

(21) Appl. No.: 17/307,367

(22) Filed: May 4, 2021

(65) Prior Publication Data

US 2021/0345683 A1    Nov. 11, 2021

(30) Foreign Application Priority Data

May 5, 2020    (DE) .......................... 102020112095.8

(51) Int. Cl.
*G06K 19/077*    (2006.01)
*A24F 40/10*    (2020.01)
*A24F 40/53*    (2020.01)
*A24F 40/65*    (2020.01)
*A24F 40/70*    (2020.01)

(52) U.S. Cl.
CPC .............. *A24F 40/53* (2020.01); *A24F 40/10* (2020.01); *A24F 40/65* (2020.01); *A24F 40/70* (2020.01)

(58) Field of Classification Search
CPC ............ G06K 19/07747; G06K 19/077; A24F 40/53; A24F 40/10; A24F 40/40
See application file for complete search history.

(56) References Cited

U.S. PATENT DOCUMENTS

| 4,994,659 A * | 2/1991 | Yabe ................ G06K 19/07745 235/492 |
| 2017/0042224 A1* | 2/2017 | Murison ................ G01K 13/02 |
| 2020/0114094 A1 | 4/2020 | Atkins et al. |

OTHER PUBLICATIONS

German Patent Office, Office Action issued for DE 102020112095.8, 4 pgs., dated Dec. 21, 2020.

* cited by examiner

*Primary Examiner* — Hae Moon Hyeon
(74) *Attorney, Agent, or Firm* — Banner & Witcoff Ltd.

(57) ABSTRACT

An electronic inhalation apparatus including a body having a chip module accommodating region which is at least partially surrounded by a folding structure. When a chip module is accommodated in the chip module accommodating region, the folding structure is bent around the chip module in order to fasten the chip module.

19 Claims, 9 Drawing Sheets

FIG. 4A
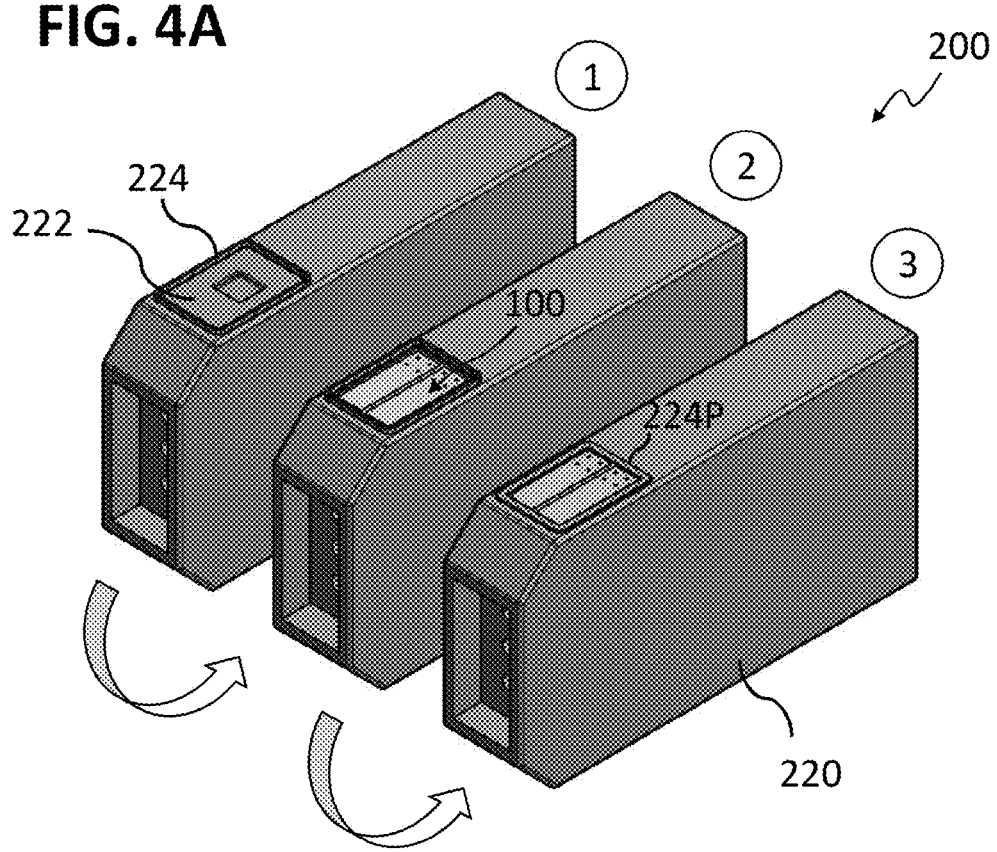
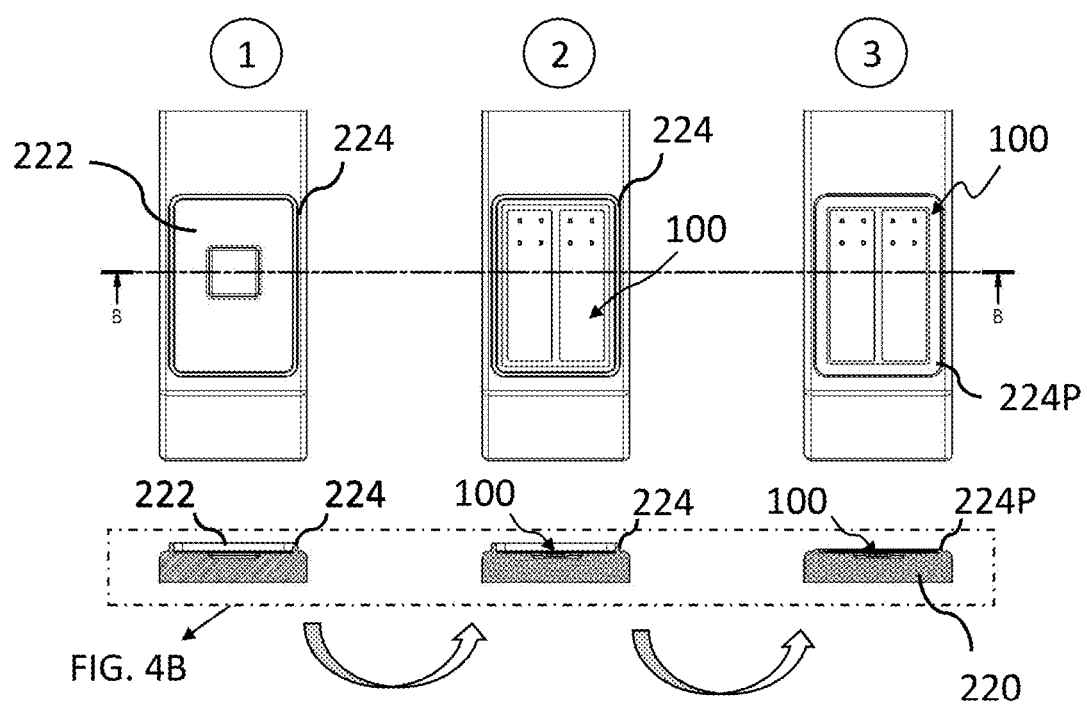
FIG. 4B

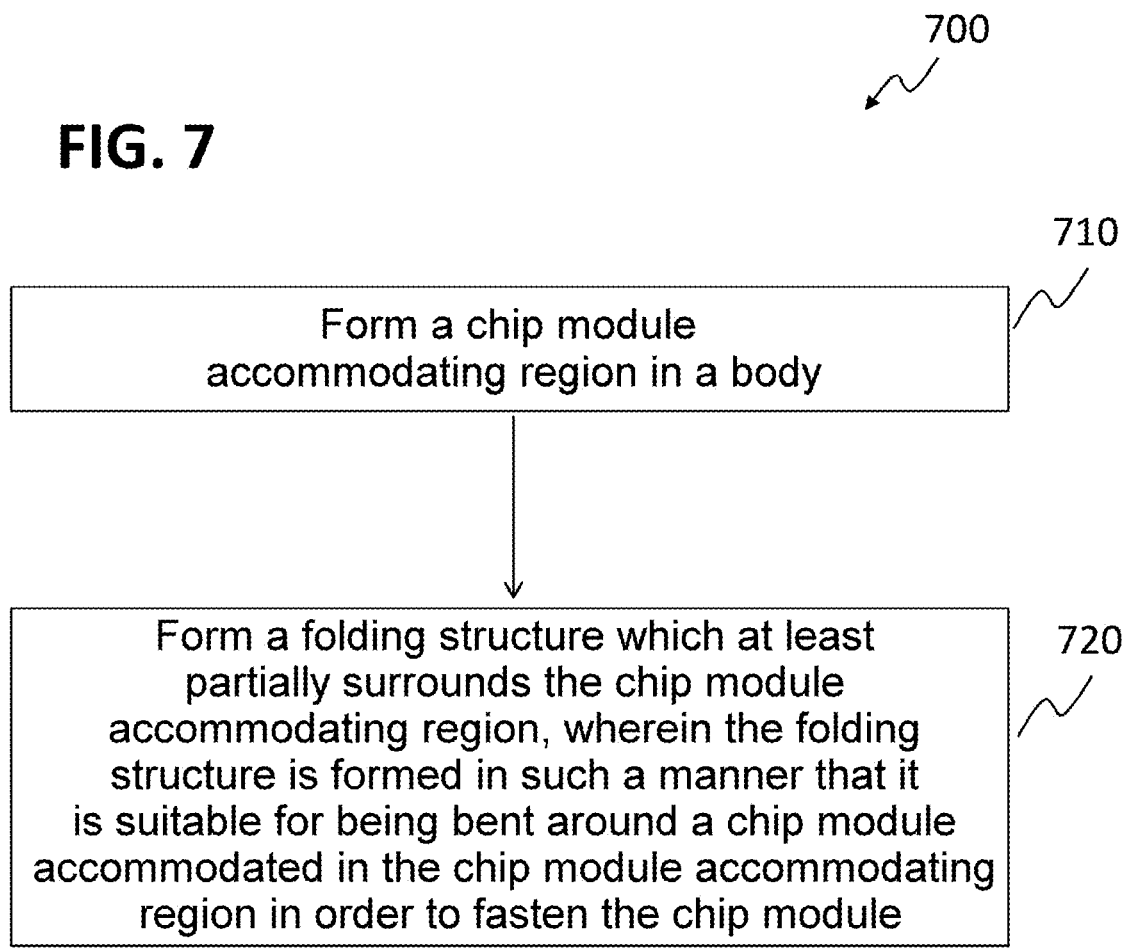

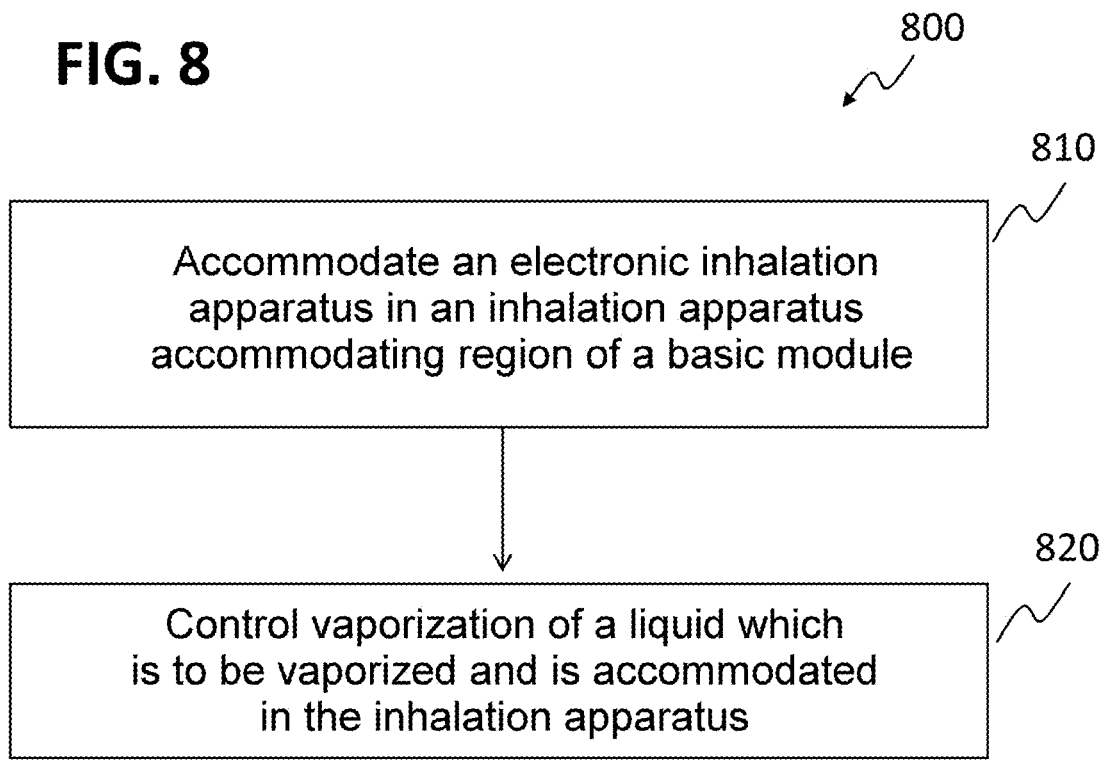

ELECTRONIC INHALATION APPARATUS WITH A CHIP MODULE FIXED WITH A FOLDING STRUCTURE

(B) CROSS-SECTION TO RELATED APPLICATIONS

Not Applicable.

(C) STATEMENT REGARDING FEDERALLY SPONSORED RESEARCH OR DEVELOPMENT

Not Applicable.

(D) THE NAMES OF THE PARTIES TO A JOINT RESEARCH AGREEMENT

Not applicable.

(E) INCORPORATION-BY-REFERENCE OF MATERIAL SUBMITTED ON A REAL-ONLY OPTICAL DISC, AS A TEXT FILE OR AN XML FILE VIA THE PATENT ELECTRONIC SYSTEM

Not applicable.

(F) STATEMENT REGARDING PRIOR DISCLOSURES BY THE INVENTOR OR A JOINT INVENTOR

Not applicable.

(G) BACKGROUND OF THE INVENTION

(1) Field of the Invention

The disclosure relates to an electronic inhalation apparatus, to an electronic inhalation device, and to a method for forming an electronic inhalation apparatus.

Electronic apparatuses having a storage container for a consumable, for example an inhalant or a toner for a printer (for example E-cigarettes), can be increasingly equipped with a chip module for authentication.

The chip module can be used to ensure, by means of the authentication, that no third-party products are used or unauthorized refilling operations are carried out. This is because this could result in failure of the apparatus or even damage to health, for example.

The apparatus containing the consumable is typically intended to be a cost-effective product, for example a disposable item. Therefore, there is a need for cost-effective production, for example for cost-effective installation of the chip module (for example the authentication module) on or in a package of the apparatus.

This means that the materials which are used to form the apparatus should be cost-effective. In addition, the chip module should also be able to be installed in or on the apparatus quickly and easily, with the result that a high throughput can be achieved using cost-effective installation devices.

In a currently used installation method, the chip module is firmly stuck to an apparatus body by means of an ultraviolet (UV)-curing adhesive. In this case, a high throughput can be achieved and a thermal load for the apparatus body and the chip module is low.

However, there is the risk of the UV-curing adhesive not curing completely if the adhesive (arranged between the chip module and the apparatus body) is not fully reached by UV light. A considerably more complex procedure is needed to ensure reliable adhesive bonding.

(2) Description of Related Art including information disclosed under 37 CFR 1.97 and 1.98.

Not Applicable.

(H) BRIEF SUMMARY OF THE INVENTION

Various exemplary aspects provide an electronic inhalation apparatus which has a chip module accommodating region having a folding structure which at least partially surrounds the chip module accommodating region. The folding structure is formed in such a manner that it can be bent around the chip module after the chip module has been arranged in the chip module accommodating region.

Various exemplary aspects provide an electronic inhalation apparatus and a method for producing the latter which comprises shaping a material of the electronic inhalation apparatus in order to fasten the chip module to or in a body of the electronic inhalation apparatus. Accordingly, it is possible to dispense with additional fastening materials, for example adhesives.

(H) BRIEF DESCRIPTION OF THE SEVERAL VIEWS OF THE DRAWINGS

Exemplary aspects of the disclosure are illustrated in the figures and are explained in more detail below.

Figure 3A:
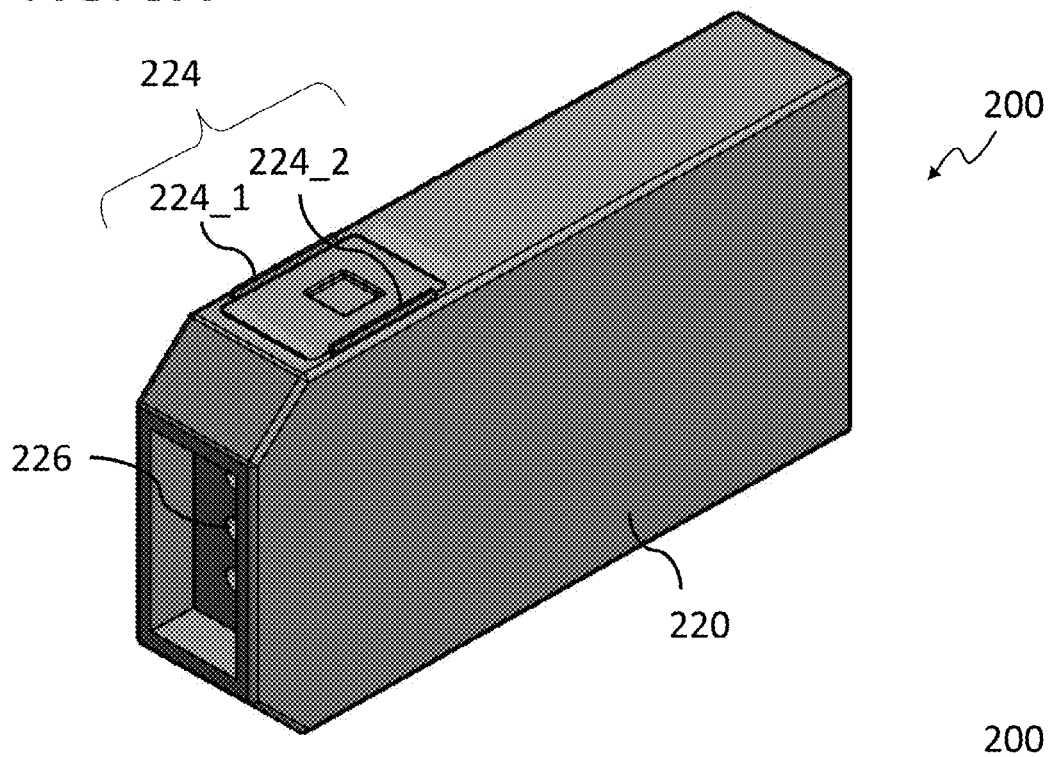
Figure 3B:
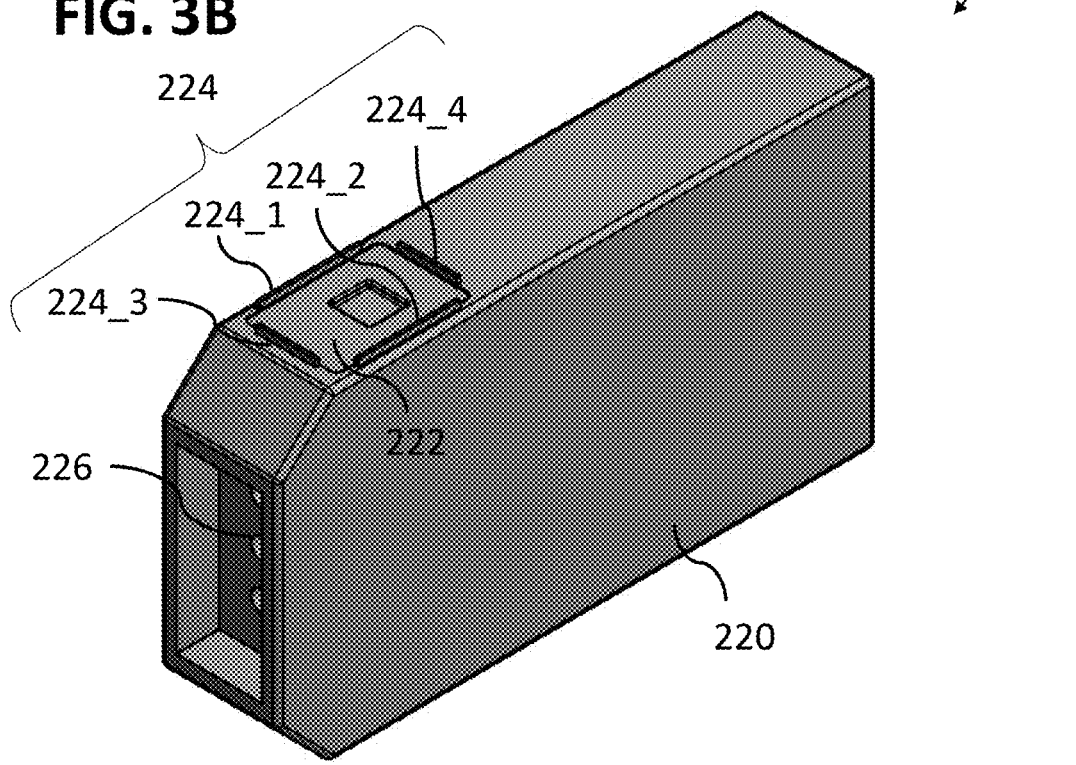
Figure 4B:
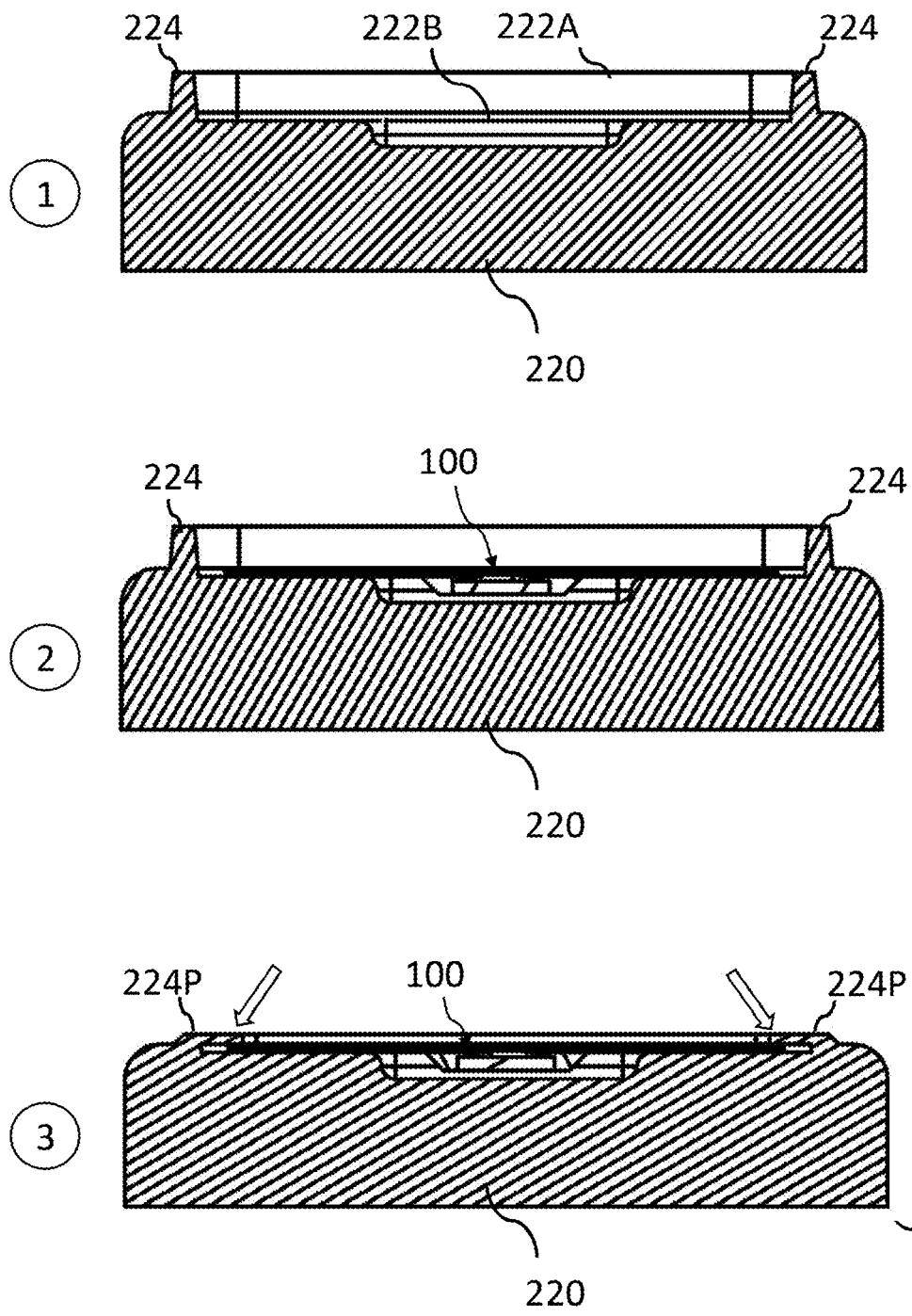
Figure 5:
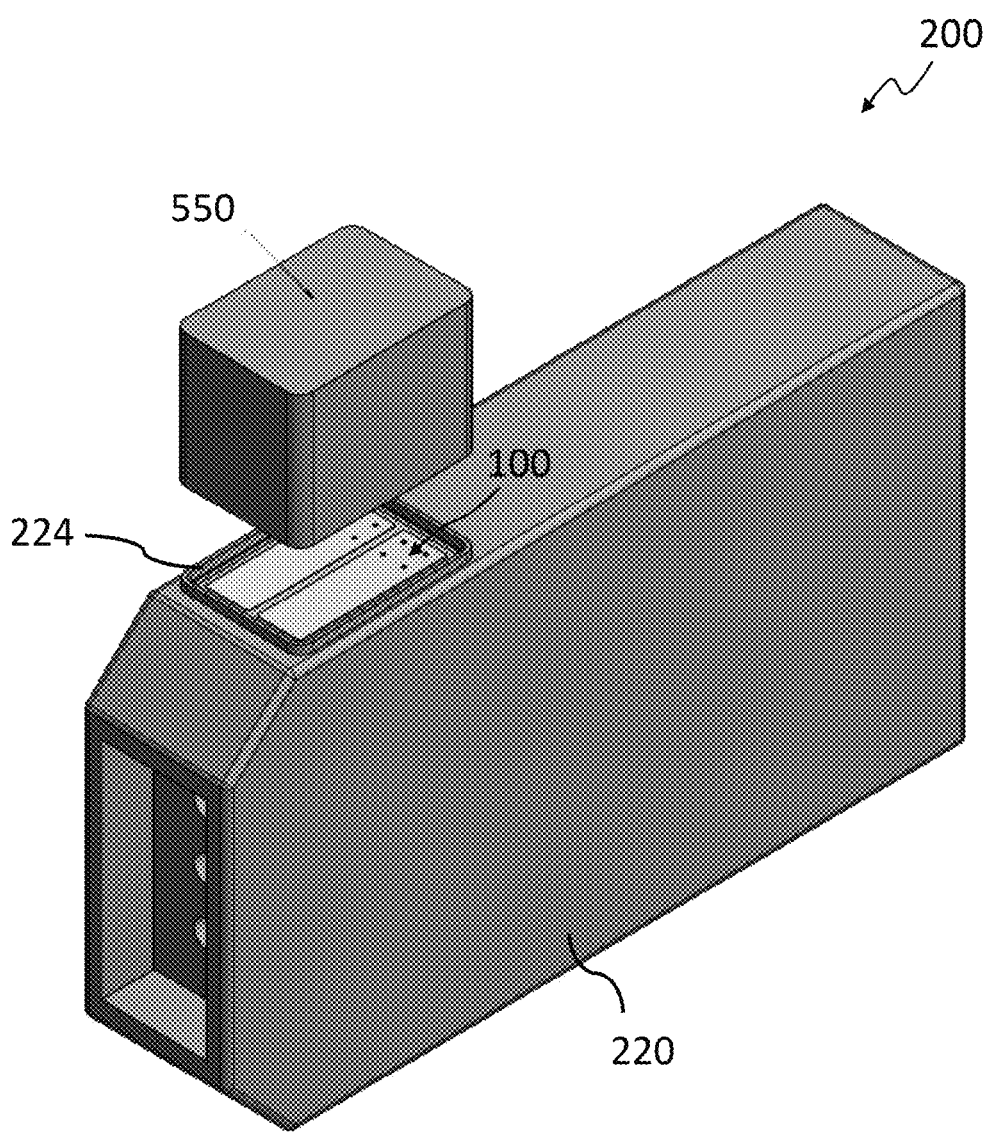
Figure 6:
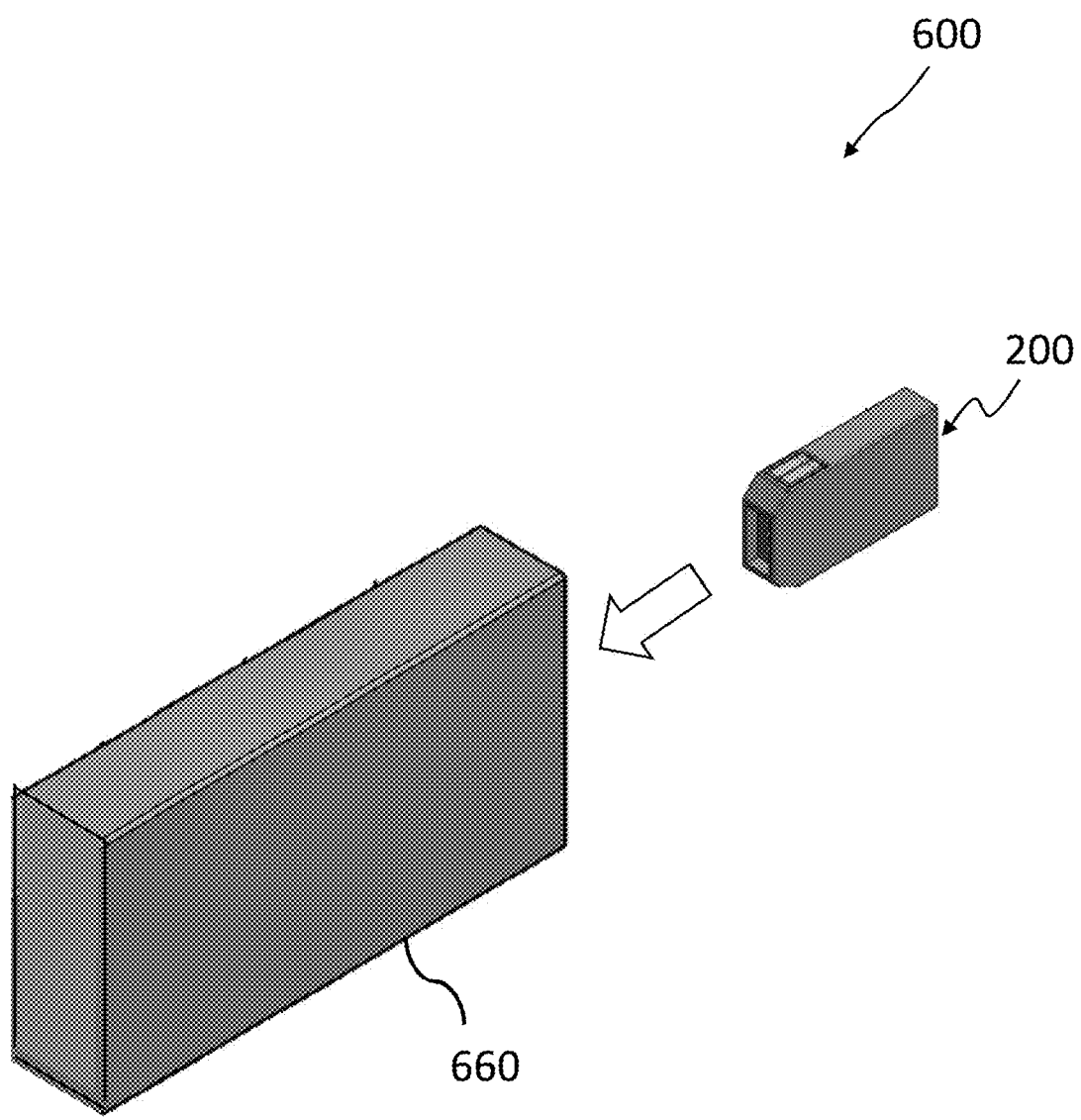

FIG. 3A and FIG. 3B each show a schematic perspective illustration of an electronic inhalation apparatus according to various exemplary aspects;

FIG. 4A and FIG. 4B show an illustration of a process of installing a chip module of an electronic inhalation apparatus according to various exemplary aspects;

FIG. 5 shows an illustration of a process of installing a chip module of an electronic inhalation apparatus according to various exemplary aspects;

FIG. 6 shows a schematic perspective illustration of an electronic inhalation device according to various exemplary aspects;

FIG. 7 shows a flowchart of a method for forming an electronic inhalation apparatus according to various exemplary aspects; and FIG. 8 shows a flowchart of a method for operating an electronic inhalation device according to various exemplary aspects.

(I) DETAILED DESCRIPTION OF THE INVENTION

In the following detailed description, reference is made to the accompanying drawings which form part of said description and show, for illustration, specific aspects in which the subject matter of the disclosure can be performed. In this respect, direction terminology, for instance "at the top", "at the bottom", "at the front", "at the rear", "front", "rear", etc., is used with reference to the orientation of the described figure(s). Since components of aspects can be positioned in a number of different orientations, the direction terminology is used for illustration and is not restrictive in any way. It goes without saying that other aspects can be used and structural or logical changes can be made without departing from the scope of protection of the present disclosure. It goes without saying that the features of the various exemplary aspects described herein can be combined with one another, unless specifically stated otherwise. The following detailed description therefore should not be interpreted in a restrictive sense, and the scope of protection of the present disclosure is defined by the attached claims.

Within the scope of this description, the terms "linked", "connected" and "coupled" are used to describe both a direct and an indirect link, a direct or indirect connection and direct or indirect coupling. In the figures, identical or similar elements are provided with identical reference signs if expedient.

Figure 1:
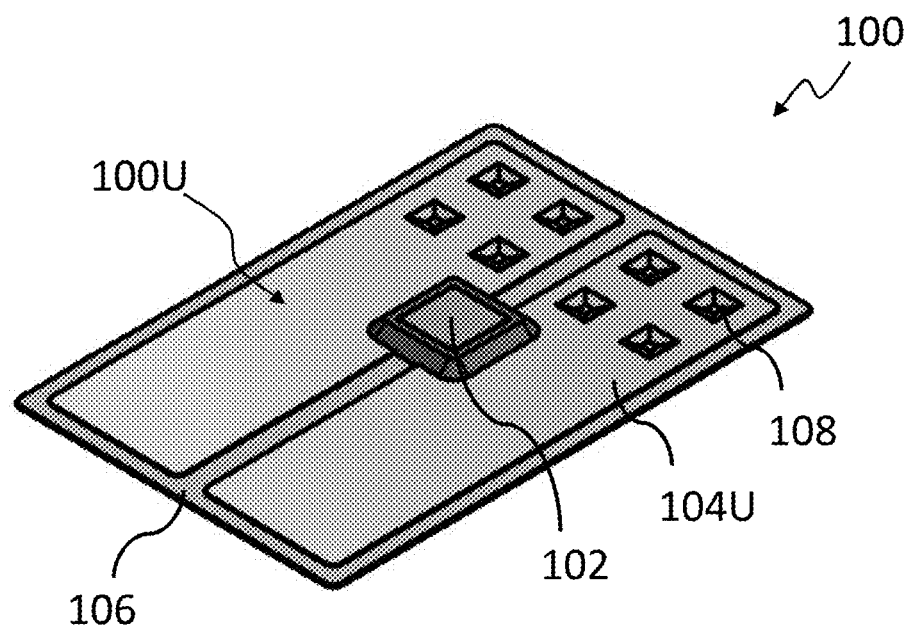
FIG. 1 shows a schematic perspective illustration of a chip module for an electronic inhalation apparatus according to various exemplary aspects.
Figure 1:
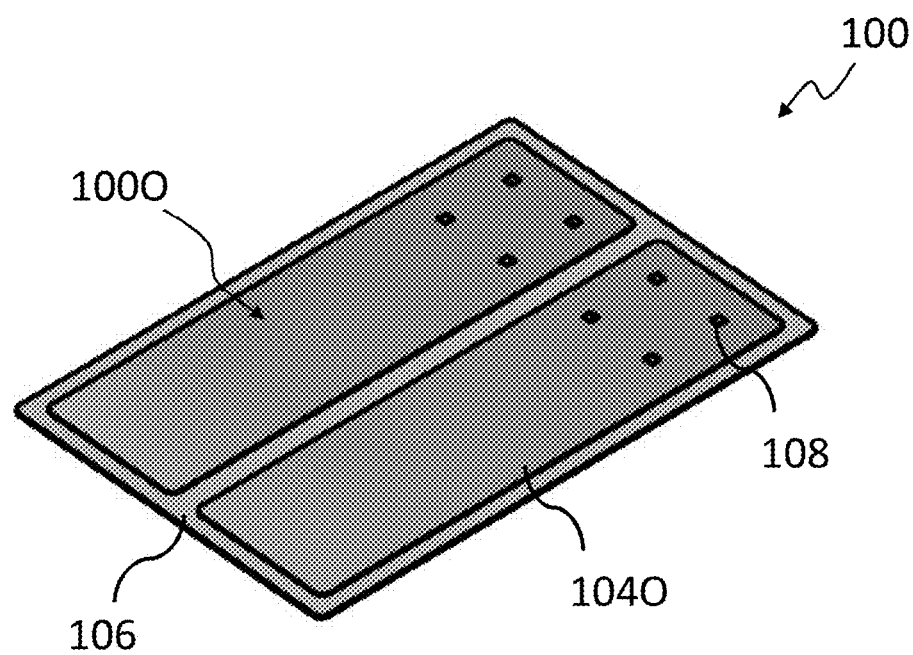
Figure 2:
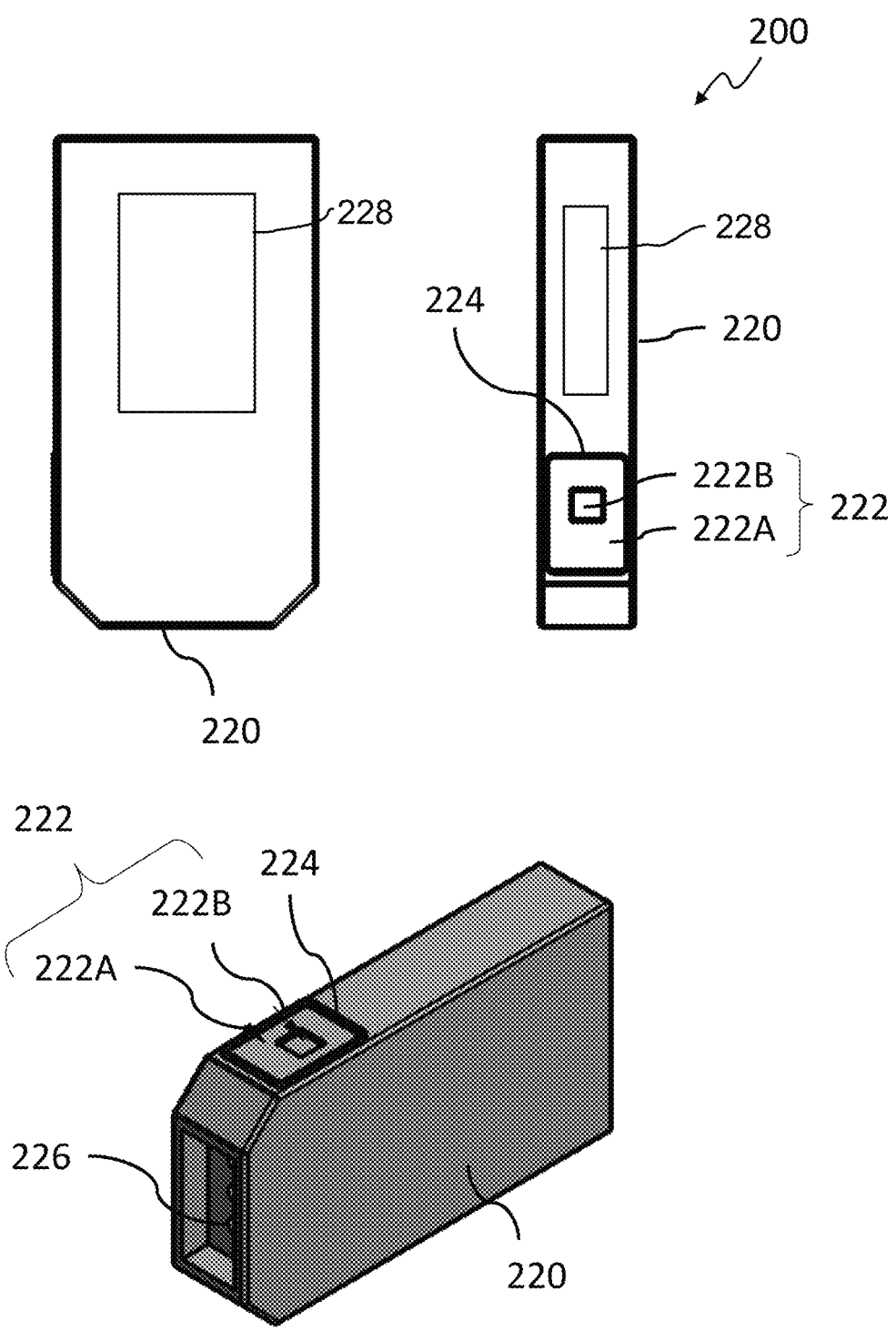
FIG. 2 shows various schematic views of an electronic inhalation apparatus according to various exemplary aspects.

FIG. 1 shows a schematic perspective illustration of a chip module 100 (a view of its underside 100U at the top and a view of its top side 100O at the bottom) for an electronic inhalation apparatus 200 according to various exemplary aspects. FIG. 2 shows various schematic views of an electronic inhalation apparatus 200 according to various exemplary aspects. FIGS. 3A and 3B each show a schematic perspective illustration of an electronic inhalation apparatus 200 according to various exemplary aspects. FIGS. 4A and 4B show an illustration of a process of installing a chip module 100 of an electronic inhalation apparatus 200 according to various exemplary aspects, and FIG. 5 shows an illustration of a process of installing a chip module 100 of an electronic inhalation apparatus 200 according to various exemplary aspects.

Various exemplary aspects provide an electronic inhalation apparatus 200 (for short: inhalation apparatus), for example a pod for an E-cigarette.

The electronic inhalation apparatus 200 may have a body 220 having a chip module accommodating region 222.

The body 220 may have, for example, a chamber or a cavity 228 which can be used to accommodate an inhalation liquid.

In various exemplary aspects, the body 220 may have or is composed of a thermoplastic, for example polystyrene, polypropylene (PP), polyethylene (PE), polyethylene terephthalate (PET) or others, depending on the application (for example depending on whether chemical insensitivity to a product which is poured into the chamber and/or medical harmlessness is/are required). The body 220 may have been or may be formed by means of injection molding, for example.

In order to use the inhalation apparatus 200 for inhalation, the inhalation apparatus 200 may be able to be coupled or may be coupled to a basic module 660 (see FIG. 6).

The basic module 660 may have an inhalation apparatus accommodating region (not illustrated), in which the electronic inhalation apparatus 200 has been or is or can be accommodated, and a control circuit which is configured to control vaporization of a liquid which is to be vaporized and is accommodated in the inhalation apparatus 200.

The basic module 660 may form, with the inhalation apparatus 200, in various exemplary aspects, an electronic inhalation device 600 (for short: inhalation device).

For the purpose of supplying energy to and controlling the installation apparatus 200, the inhalation apparatus 200 may have connection contacts 226 which can be connected in an electrically conductive manner to the basic module 660, for example by means of corresponding mating contacts in the basic module 660.

The basic module 660 may also have an authentication circuit (not illustrated) for authenticating the inhalation apparatus 200 and a communication interface (not illustrated) for communicating with the chip module 100 of the inhalation apparatus 200 in a contactless or contact-based manner. The communication interface may be coupled, for example connected in an electrically conductive manner, to the control circuit.

The inhalation device 600 may be configured to enable use of the inhalation device 600 for inhalation only after positive authentication of the inhalation apparatus 200 (or a chip module 100 fitted to it or integrated in it).

The accommodating region 222 may have a flatter first accommodating subregion 222A which can be used to accommodate a carrier 106. The carrier 106 may have or be composed of polyethylene terephthalate (PET), polyimide (PI) and/or an epoxy material, for example.

Metal surfaces 104O, 104U may be arranged on mutually opposite main surfaces on the carrier 106. In the exemplary aspect illustrated, there are two metal surfaces 104 in each case; depending on the application, there may be a different number, for example three contact surfaces for VCC (supply voltage), VSS (source voltage) and SWI (Single Wire Interface data line) for contact-based communication.

The metal surfaces 104U arranged on an underside 100U of the chip module 100 can be connected in an electrically conductive manner to the chip 102, and the metal surfaces 104O arranged on a top side 100O of the chip module 100 can be connected in an electrically conductive manner to the lower metal surfaces 104U, for example by means of vias 108.

The upper and lower metal surfaces 104O and 104U can be used to provide communication between the basic module 660 and the chip module 100, for example contactless communication, for example by means of capacitive interaction, or contact-based communication. In addition, the chip 102 can be supplied with energy by means of the upper and lower metal surfaces 104O and 104U.

The accommodating region 222 may have (if the chip module 100 is configured such that the chip 102 forms a projection) a second accommodating subregion 222B which extends deeper into the body 220 from the first accommodating subregion 222A. This makes it possible for the carrier 106 to terminate in a flat manner with a surface of the chip module 100 and for the carrier 106 to nevertheless lie in the accommodating region 222.

The second accommodating subregion 222B may be configured to accommodate a chip 102 installed on the carrier 106. The chip 102 may be an integrated circuit (IC). The chip 102 may be installed on the carrier 106 by means of flip-chip technology.

The accommodating region 222 may be at least partially surrounded by a folding structure 224 which, when the chip module 100 is accommodated in the chip module accommodating region 222, has been or is bent around the chip module 100 in order to fasten the chip module 100.

In various exemplary aspects, the folding structure 224 may be formed as a raised structure on or in a surface of the body 220 adjoining the accommodating region 222.

In various exemplary aspects, the folding structure 224 may be formed completely or partially in one piece with the body 220, for example may have been formed or may be formed during injection molding of the body.

In various exemplary aspects, the folding structure 224 may have been or may be fastened completely or partially to the body 220, for example may have been or may be adhesively bonded on or welded on.

The folding structure 224 may have or be composed of a thermoplastic, for example polystyrene.

The folding structure 224 may have the same material as the body 220. This applies both to the one-piece aspect (for example by means of multi-component injection molding) and to the aspect composed of a plurality of components (body 220 and folding structure 224).

The folding structure 224 may have a different material to the body 220. This applies both to the one-piece aspect and to the aspect composed of a plurality of components (body 220 and folding structure 224).

The folding structure 224 is provided in order to make it possible to easily fasten the chip module 100 to/in the body 220, for example in the chip module accommodating region 222.

In various exemplary aspects, for example if the folding structure 224 is used only to assist with fastening the chip module 100, for example if the chip module 100 is additionally adhesively bonded in the chip module accommodating region 222, it may already be sufficient to provide the folding structure 224 only on one side of the chip module accommodating region 222, for example. In that case, the folding structure 224, after being bent around, can clamp the chip module 100 in a sufficiently firm manner in order to prevent forces from acting on the adhesive bond, which forces could result in the adhesive bond being detached.

In various exemplary aspects, the folding structure 224 may have or be composed of a plurality of folding regions 224_1, 224_2, . . . , for example a segmented ring.

In various exemplary aspects, the folding structure 224 may respectively have a folding region 224_1 and 224_2 on two mutually opposite sides of the chip module accommodating region 222. This is illustrated, by way of example, in FIG. 3A. Such a folding structure 224 may be suitable, for example, as the sole fastening of the chip module in the chip module accommodating region 222.

In various exemplary aspects, the folding structure 222 may respectively have a folding region 224_1, 224_2, 224_3, 224_4 on each side of the chip module accommodating region 222. This is illustrated, by way of example, in FIG. 3B. This enables even more reliable fastening than with only two mutually opposite folding regions 224_1, 224_2.

In various exemplary aspects, the folding structure 224 may be guided completely or substantially completely around the chip module accommodating region 222, for example in an annular manner. This is illustrated, by way of example, in FIG. 2 and FIG. 4A.

In various exemplary aspects, the chip module 100 can be arranged in the chip module accommodating region 222, and the folding structure 224 for fastening the chip module 100 may be bent around the chip module 100. The folding structure 224 may clamp the chip module 100 in the chip module accommodating region 222.

In various exemplary aspects, the chip module 100 may be additionally fastened in the chip module accommodating region 222 by means of an adhesive, for example by means of a cyanoacrylate adhesive (not illustrated). This can substantially serve the purpose of connecting the chip 102 to the body 220 in such a manner that the chip module 100 or the chip 102 cannot be detached from the body 220 without destruction.

The chip module 100 can then be configured to authenticate the inhalation apparatus 200 with respect to a control circuit which is configured to control vaporization of a liquid which is to be vaporized and is accommodated in the inhalation apparatus 200. If the chip module 100 or the chip 102 could be detached from the body 220, it could possibly be transferred to another inhalation apparatus.

In that case, requirements imposed on a quality of the adhesive bond may be lower than in the case in which the chip module 100 is fastened in the chip module accommodating region 222 solely by means of an adhesive.

A sequence of the process of fastening the chip module 100 to the body 220 of the inhalation apparatus 200 is respectively illustrated in FIG. 4A and FIG. 4B.

In the views marked with a 1 (at the top: perspective view, in the center: plan view of the accommodating region 222, at the bottom and enlarged in FIG. 4B: cross-sectional view), the body 220 having the chip module accommodating region 222 is provided.

In the view marked with a 2, the body 220 having the chip module 100 arranged in the chip module accommodating region 222 is provided.

In the view marked with a 3, the body 220 having the bent folding structure 224P is illustrated. The chip module 100 can be fastened to the body 220 in a clamped manner by means of the bent folding structure 224P.

The shaping of the folding structure 224P (for example bending or pressing) can be carried out in various exemplary aspects by means of a shaping tool 550.

The shaping tool 550 may be configured to shape the folding structure 224P by means of pressure (die) and/or temperature (thermode) and/or ultrasound (ultrasonic transducer) and/or irradiation (laser). In this case, the folding structure 224 may be shaped in the direction of the chip module 100. In various exemplary aspects, combinations of these processes and/or further suitable processes can be used.

The body 220 may be formed below the chip module accommodating region 222 in such a manner that it does not suffer any (unforeseen) damage as a result of the shaping, for example by means of the shaping tool 550.

For example, in a case in which ultrasound is used during shaping, a supporting structure may be formed below the chip module accommodating region in order to prevent local vibrations of the body 220 during shaping of the folding structure 224.

In various exemplary aspects, a precise shape of the shaped folding structure 224P may have been defined or may be defined by a shape of the shaping tool 550, for example a shape of its underside which may be in contact with the folding structure 224 during shaping.

Depending on a required shape of the shaped folding structure 224P, the shaping can be carried out as a single process, in which the shaped folding structure 224P is simultaneously brought into the definitive shape during shaping, or as a multi-stage process, in which, for example, the shaped folding structure 224P is formed in a first shaping process and the shaped folding structure 224P is smoothed or flattened in a second shaping process.

In FIG. 4A and FIG. 4B, the chip module 100 is fastened in such a manner that its exposed surface, for example the metal surface 1080, forms a common plane with a surrounding surface of the inhalation apparatus 200.

In various exemplary aspects, depending on requirements, the chip module 100 may be fastened or may have been fastened in such a manner that its exposed surface, for example the metal surface 1080, is above or below the surrounding surface of the inhalation apparatus 200.

In various exemplary aspects, the shaped folding structure 224P can (for example only) mechanically fasten the chip module 100, for example may be arranged in a form-fitting manner and/or may at least partially cover the chip module 100. Such covering regions are marked in FIG. 4B with arrows in view 3.

In various exemplary aspects, the shaped folding structure 224P can alternatively or additionally form a material bond, for example can act as a bonding agent. In other words, the shaped folding structure 224P can act like a thermoplastic hot adhesive. In that case, the shaped folding structure 224P can adhere to the chip module 100 or can be connected to the carrier 106 of the chip module 100 during fusing, for example. For this purpose, it may be necessary for the carrier 106 of the chip module 100 to have a suitable material or to at least be coated with a suitable material.

Exemplary aspects in which adhesion and/or connection of the body 220 to the carrier 106 is produced during shaping may be advantageous, in particular, in cases in which an underside 100U of the chip module 100 is intended to be sealed with respect to an environment, for example owing to a field of use which could be harmful for the chip module 100 or the chip 102.

A further advantage is that a connection which cannot be detached without destruction is formed in this manner between the chip module 100 and the body 220, thus producing a forgery-proof product.

In various exemplary aspects, simple, cost-effective and reliable fastening for a chip module 100 to a body 220 of an inhalation apparatus 200 is provided.

FIG. 7 shows a flowchart 700 of a method for forming an electronic inhalation apparatus according to various exemplary aspects.

The method comprises forming a chip module accommodating region in a body (710) and forming a folding structure which at least partially surrounds the chip module accommodating region, wherein the folding structure is formed in such a manner that it is suitable for being bent around a chip module accommodated in the chip module accommodating region in order to fasten the chip module (720).

FIG. 8 shows a flowchart 800 of a method for operating an electronic inhalation device according to various exemplary aspects.

The method comprises accommodating an electronic inhalation apparatus according to one of the exemplary aspects in an inhalation apparatus accommodating region of a basic module (810) and controlling vaporization of a liquid which is to be vaporized and is accommodated in the inhalation apparatus (820).

Some exemplary aspects are stated in summary below.

Exemplary aspect 1 is an electronic inhalation apparatus. The electronic inhalation apparatus has a body having a chip module accommodating region which is at least partially surrounded by a folding structure which, when a chip module is accommodated in the chip module accommodating region, is bent around the chip module in order to fasten the chip module.

Exemplary aspect 2 is an electronic inhalation apparatus according to exemplary aspect 1, wherein the folding structure respectively has a folding region on two mutually opposite sides of the chip module accommodating region.

Exemplary aspect 3 is an electronic inhalation apparatus according to exemplary aspect 1 or 2, wherein the folding structure respectively has a folding region on each side of the chip module accommodating region.

Exemplary aspect 4 is an electronic inhalation apparatus according to one of exemplary aspects 1 to 3, also having: the chip module which is arranged in the chip module accommodating region, wherein the folding structure is bent around the chip module in order to fasten the chip module.

Exemplary aspect 5 is an electronic inhalation apparatus according to exemplary aspect 4, wherein the chip module is clamped in the chip module accommodating region.

Exemplary aspect 5 is an electronic inhalation apparatus according to exemplary aspect 4, wherein the chip module is fastened in the chip module accommodating region by means of an adhesive.

Exemplary aspect 6 is an electronic inhalation apparatus according to exemplary aspect 4 or 5, wherein the chip module is configured to authenticate the inhalation apparatus with respect to a control circuit which is configured to control vaporization of a liquid which is to be vaporized and is accommodated in the inhalation apparatus.

Exemplary aspect 7 is an electronic inhalation apparatus according to exemplary aspect 6, wherein the chip module has a contactless communication apparatus for contactless data interchange and is configured to carry out the authentication by means of the contactless communication apparatus.

Exemplary aspect 8 is an electronic inhalation apparatus according to one of exemplary aspects 1 to 7, which also has a chamber for accommodating a liquid to be vaporized.

Exemplary aspect 9 is an electronic inhalation apparatus according to one of exemplary aspects 1 to 8, wherein the folding structure is formed in one piece with the body.

Exemplary aspect 10 is an electronic inhalation apparatus according to one of exemplary aspects 1 to 9, wherein the folding structure is fastened to the body.

Exemplary aspect 11 is an electronic inhalation apparatus according to one of exemplary aspects 1 to 10, wherein the folding structure has or is composed of a thermoplastic, for example polystyrene.

Exemplary aspect 12 is an electronic inhalation device which has an electronic inhalation apparatus according to one of exemplary aspects 1 to 11 and a basic module having an inhalation apparatus accommodating region, in which the electronic inhalation apparatus is accommodated, and a control circuit which is configured to control vaporization of a liquid which is to be vaporized and is accommodated in the inhalation apparatus.

Exemplary aspect 13 is an electronic inhalation apparatus according to one of exemplary aspects 1 to 11, wherein the electronic inhalation apparatus is an E-cigarette.

Exemplary aspect 14 is a method for forming an electronic inhalation apparatus. The method comprises forming a chip module accommodating region in a body and forming a folding structure which at least partially surrounds the chip module accommodating region, wherein the folding structure is formed in such a manner that it is suitable for being bent around a chip module accommodated in the chip module accommodating region in order to fasten the chip module.

Exemplary aspect 15 is a method according to exemplary aspect 14, wherein the formation of the folding structure comprises respectively forming a folding region on two mutually opposite sides of the chip module accommodating region.

Exemplary aspect 16 is a method according to exemplary aspect 14 or 15, wherein the folding structure respectively has a folding region on each side of the chip module accommodating region.

Exemplary aspects 17 is a method according to one of exemplary aspects 14 to 16, which also comprises arranging a chip module in the chip module accommodating region, and bending the folding structure around the chip module in order to fasten the chip module, with the result that the chip module is clamped in the chip module accommodating region.

Exemplary aspect 18 is a method according to exemplary aspect 17, wherein the bending comprises thermal deformation, for example by means of a welding die.

Exemplary aspect 19 is a method according to exemplary aspect 17 or 18, which also comprises arranging an adhesive in the chip module accommodating region before arranging the chip module.

Exemplary aspect 20 is a method according to one of exemplary aspects 17 to 19, which also comprises authenticating the inhalation apparatus with respect to a control circuit which is configured to control vaporization of a liquid which is to be vaporized and is accommodated in the inhalation apparatus.

Exemplary aspect 21 is a method according to exemplary aspect 20, wherein the authentication is carried out by means of contactless communication.

Exemplary aspect 22 is a method according to one of exemplary aspects 14 to 21, which the inhalation apparatus also has a chamber for accommodating a liquid to be vaporized.

Exemplary aspect 23 is a method according to one of exemplary aspects 14 to 22, wherein the folding structure is formed at the same time as the formation of the body and the chip module accommodating region.

Exemplary aspect 24 is a method according to exemplary aspect 23, wherein the body having the chip module accommodating region and the folding structure is formed by means of injection molding.

Exemplary aspect 25 is a method according to one of exemplary aspects 14 to 24, wherein the formation of the folding structure comprises fastening at least one folding structure element to the body.

Exemplary aspect 26 is a method according to one of exemplary aspects 14 to 25, wherein the folding structure has or is composed of a thermoplastic, for example polystyrene.

Exemplary aspect 27 is a method for operating an electronic inhalation device, which comprises accommodating an electronic inhalation apparatus according to one of exemplary aspects 1 to 11 or 13 in an inhalation apparatus accommodating region of a basic module and controlling vaporization of a liquid which is to be vaporized and is accommodated in the inhalation apparatus.

Further advantageous configurations of the apparatus emerge from the description of the method and vice versa.

(m) Sequence Listing.

Not applicable.

The invention claimed is:

1. An electronic inhalation apparatus, comprising:
a body having a chip module accommodating region that is at least partially surrounded by a folding structure which, when a chip module is accommodated in the chip module accommodating region, is bent around the chip module in order to fasten the chip module, wherein the folding structure respectively has a folding region on each side of the chip module accommodating region.

2. The electronic inhalation apparatus as claimed in claim 1,
wherein the folding structure respectively has a folding region on two mutually opposite sides of the chip module accommodating region.

3. The electronic inhalation apparatus as claimed in claim 1,
wherein the chip module is arranged in the chip module accommodating region, and the folding structure is bent around the chip module in order to fasten the chip module.

4. The electronic inhalation apparatus as claimed in claim 3,
wherein the chip module is clamped in the chip module accommodating region.

5. The electronic inhalation apparatus as claimed in claim 3,
wherein the chip module is fastened in the chip module accommodating region by means of an adhesive.

6. The electronic inhalation apparatus as claimed in claim 3,
wherein the chip module is configured to authenticate the inhalation apparatus with respect to a control circuit which is configured to control vaporization of a liquid which is to be vaporized and is accommodated in the inhalation apparatus.

7. The electronic inhalation apparatus as claimed in claim 6,
wherein the chip module has a contactless communication apparatus for contactless data interchange and is configured to carry out the authentication by means of the contactless communication apparatus.

8. The electronic inhalation apparatus as claimed in claim 1, further comprising:
a chamber configured to accommodate a liquid to be vaporized.

9. The electronic inhalation apparatus as claimed in claim 1,
wherein the folding structure is formed in one piece with the body.

10. The electronic inhalation apparatus as claimed in claim 1,
wherein the folding structure is fastened to the body.

11. The electronic inhalation apparatus as claimed in claim 1,
wherein the folding structure has or is composed of polystyrene.

12. An electronic inhalation device, comprising:
an electronic inhalation apparatus as claimed in claim 1; and
a basic module having an inhalation apparatus accommodating region in which the electronic inhalation apparatus is accommodated, and a control circuit which is configured to control vaporization of a liquid which is to be vaporized and is accommodated in the inhalation apparatus.

13. The electronic inhalation apparatus as claimed in claim 1,
wherein the electronic inhalation apparatus is an E-cigarette.

14. A method for forming an electronic inhalation apparatus, comprising:
forming a chip module accommodating region in a body; and
forming a folding structure which at least partially surrounds the chip module accommodating region, wherein the folding structure is formed to be bendable around a chip module accommodated in the chip module accommodating region in order to fasten the chip module, wherein the folding structure respectively has a folding region on each side of the chip module accommodating region.

15. The method as claimed in claim 14, further comprising:
- arranging the chip module in the chip module accommodating region; and
- bending the folding structure around the chip module in order to fasten the chip module, with the result that the chip module is clamped in the chip module accommodating region.

16. The method as claimed in claim 15,
- wherein the bending comprises thermal deformation by means of a welding die.

17. The method as claimed in claim 15, further comprising:
- arranging an adhesive in the chip module accommodating region before arranging the chip module.

18. The method as claimed in claim 14,
- wherein the folding structure is formed at the same time as the formation of the body and the chip module accommodating region.

19. The method as claimed in claim 18,
- wherein the body having the chip module accommodating region and the folding structure is formed by means of injection molding.

\* \* \* \* \*